US010307453B2

(12) United States Patent
Gong et al.

(10) Patent No.: US 10,307,453 B2
(45) Date of Patent: Jun. 4, 2019

(54) METHOD FOR EXTRACTING STILBENE COMPOUNDS

(71) Applicant: KPC PHARMACEUTICALS, INC, Yunnan (CN)

(72) Inventors: Yunqi Gong, Yunnan (CN); Jinxin Chen, Yunnan (CN); Fang Fang, Yunnan (CN)

(73) Assignee: KPC PHARMACEUTICALS, INC, Kunming, Yunnan (CN)

(*) Notice: Subject to any disclaimer, the term of this patent is extended or adjusted under 35 U.S.C. 154(b) by 70 days.

(21) Appl. No.: 15/527,933

(22) PCT Filed: Dec. 30, 2015

(86) PCT No.: PCT/CN2015/099864
§ 371 (c)(1),
(2) Date: May 18, 2017

(87) PCT Pub. No.: WO2016/110216
PCT Pub. Date: Jul. 14, 2016

(65) Prior Publication Data
US 2018/0311296 A1    Nov. 1, 2018

(30) Foreign Application Priority Data
Jan. 8, 2015    (CN) .......................... 2015 1 0009725

(51) Int. Cl.
*A61K 36/708* (2006.01)
*B01D 11/02* (2006.01)

(52) U.S. Cl.
CPC ........ *A61K 36/708* (2013.01); *B01D 11/0288* (2013.01); *A61K 2236/00* (2013.01); *A61K 2236/33* (2013.01); *A61K 2236/331* (2013.01)

(58) Field of Classification Search
CPC .................................................. A61K 36/708
See application file for complete search history.

(56) References Cited

U.S. PATENT DOCUMENTS

2009/0042817 A1* 2/2009 Heger .................. A61K 9/2054
514/35
2009/0136603 A1    5/2009 Kabrodt et al.

FOREIGN PATENT DOCUMENTS

| CN | 1386500 A | 12/2002 |
|---|---|---|
| CN | 2810597 Y | 8/2006 |
| CN | 101244129 A | 8/2008 |
| CN | 101787061 A | 7/2010 |
| CN | 102579470 A | 7/2012 |
| CN | 102786563 A | 11/2012 |
| CN | 102887925 A | 1/2013 |
| CN | 102908410 A | 2/2013 |
| CN | 104262112 A | 1/2015 |
| DE | 10 2006 015 573 A1 | 10/2007 |

OTHER PUBLICATIONS

Fishman, M. et al., "Characterization of pectin, flash-extracted from orange albedo by microwave heating, under pressure", Carboyhydrate Research, 323(1-4): 126-138 (2000).
Fishman, M. et al., "Global Structure of Microwave-Assisted Flash-Extracted Sugar Beet Pectin", J. Agric. Food Chem., 56(4): 1471-1478 (2008).
Fishman, M. et al., "Physico-chemical characterization of protein-associated polysaccharides extracted from sugar beet pulp", Carboyhydratge Polymers, 92(2): 2257-2266 (2013).
Extended European Search Report for European Patent Application No. 15876716.0, dated Aug. 2, 2018, 10 pages.
International Search Report from corresponding International Patent Application No. PCT/CN2015/099864, dated Mar. 31, 2016.
Written Opinion from corresponding International Patent Application No. PCT/CN2015/099864, dated Mar. 31, 2016.
Lin, Lifeng et al.: "Study on the Extraction of Active Substances from Grape Residue," Asia Pacific Traditional Medicine, vol. 10, No. 18, Sep. 30, 2014(Sep. 30, 2014) pp. 10 and 11.
Office Action from Japanese Patent Application No. 2017-528202, dated Mar. 27, 2018.
Wang et al., "One-step Preparative Separation of Two Polyhydroxystilbenes from Rheum likiangense Sam. by High-speed Counter-current Chromatography," Phytochemical Analysis, vol. 23, Issue 6, pp. 684-688 (Nov./Dec. 2012).
First Office Action from corresponding Chinese Patent Application No. 201510009725.1, dated Mar. 4, 2019.
"Extraction and separation of astragalus compounds", Natural Medicine Chemistry. Qiu Feng., Tsinghua University press, p. 424, Aug. 31, 2013.

* cited by examiner

*Primary Examiner* — Rosanne Kosson
(74) *Attorney, Agent, or Firm* — Merchant & Gould P.C.

(57) ABSTRACT

A method for extracting stilbene compounds comprises the following steps: grinding a medicinal material rich in stilbene compounds such as *rheum officinale*; extracting the medicinal material with a herbal flash extractor for one to four times, 5-20 minutes each time; filtering and combining filtrate and concentrating the filtrate to dryness; the proportion of the medicinal material to a solvent being 1 g: 10 ml-1 g:15 ml.

9 Claims, No Drawings

METHOD FOR EXTRACTING STILBENE COMPOUNDS

This application is a National Stage Application of International Patent Application No. PCT/CN2015/099864, titled "METHOD FOR EXTRACTING STILBENE COMPOUNDS", filed 30 Dec. 2015, which claims benefit of Serial No. 201510009725.1, titled "METHOD FOR EXTRACTING STILBENE COMPOUNDS", filed 8 Jan. 2015 in the State Intellectual Property Office of the People's Republic of China and which applications are incorporated herein by reference. To the extent appropriate, a claim of priority is made to each of the above disclosed applications.

FIELD

The present invention belongs to the field of pharmaceutical chemistry. In particular, the present invention relates to a method for extracting stilbenoid compounds, and more particularly to a flash extraction method for extracting stilbenoid compounds from rhubarb.

BACKGROUND

Rhubarb is one of traditional Chinese medicinal materials in China, and a general term for various perennial plants from *Rheum*, Polygonaceae. Rhubarb is available for pharmaceutical use with rhizomes and roots thereof, and has a bitter-cold property and taste and invigorates spleen, stomach, large intestine, liver and pericardium meridian. Rhubarb exhibits an efficacy in cooling blood and stopping bleeding, draining fire and resolving toxin, promoting blood circulation and removing blood stasis, removing dampness through diuresis and removing jaundice, relieving constipation by purgation and so on. There are about 60 species of plants from *Rheum*, which are distributed in high and cold mountain areas in Asian temperate and subtropical zones. In China, there are 39 species and two varieties, which are mainly distributed in northwest, southwest and north China regions with less in northeast. In Tibetan medicines, rhubarb is classified into three grades depending on the purgation effect thereof: top, middle and low. The top grade is termed as rhubarb, the middle grade is termed as ya-rhubarb, and the low grade is termed as small-rhubarb. It has been found through research in recent years that stilbenoid compounds are characteristic components in Sect. *Rheum* plants from *Rheum*.

Stilbenoid compounds, also referred to as diphenylethylene compounds, are active ingredients extensively present in *Rheum*, Polygonaceae. It has been found through research that, stilbenoid compounds play a role in anti-aging, preventing and treating senile dementia, improving learning and memory, brain protection and neuroprotection, regulating blood lipids, anti-atherosclerosis, anti-thrombus, anti-oxidation for scavenging free radicals, protecting the nervous system, anti-tumor, lowering cholesterol, liver protection, vasodilatation and protection, skin protection, anti-depression, heart and myocardial protection, effects on diabetes, promoting hair growth, strengthening bones and so on. Among the above, activities such as anti-thrombus, skin protection, anti-depression, heart and myocardial protection, effects on diabetes, promoting hair growth, strengthening bones and so on are newly reported in recent years. Therefore, it is of very good social and economic benefits to develop and use stilbenoid compounds in rhubarb. As a result, it has been critical for the development of rhubarb to find a rapid, convenient and inexpensive method for extracting stilbenoid compounds from rhubarb.

Flash extraction is a new extraction method developed in recent years. Flash extraction is based on the principle of tissue disruption extraction, where materials are rapidly disrupted into an appropriate particle size in a flash extractor with a suitable solvent, meanwhile, high-speed stirring, super vibration, diafiltration under reduced pressure and other functions are further present in flash extraction so as to achieve the purpose of extraction. Since one extraction generally can be completed in several seconds to several minutes in flash extraction, the extraction speed thereof is more than one hundred-times of a traditional method. However, the flash extraction method employed in the prior art can only improve the extraction speed, while makes little effects on the content of active ingredients.

SUMMARY

In order to overcome the above defects existing in the prior art, an objective of the present invention is to provide a flash extraction method for extracting stilbenoid compounds, which can not only improve the extraction speed and shorten the extraction cycle, but also can increase the purity of stilbenoid compounds.

In order to achieve the objective of the present invention, the following technical solutions are employed:

A method for extracting stilbenoid compounds, comprising: using a medicinal material rich in stilbenoid compounds as a raw material, extracting in a flash extractor, filtering, combining the filtrate and concentrating to dryness.

In an embodiment of the present invention, the method for extracting stilbenoid compounds comprises: using a medicinal material rich in stilbenoid compounds as a raw material, adding a solvent after pulverizing the medicinal material, extracting one to four times in a flash extractor for 5-20 minutes each time, filtering, combining the filtrate and concentrating to dryness.

In a preferred embodiment of the present invention, the weight-to-volume ratio in g/ml of the medicinal material to the solvent is 1:10-1:15.

In an embodiment of the present invention, in the method for extracting stilbenoid compounds according to the present invention, the medicinal material rich in stilbenoid compounds is one or a mixture of more than two of *Rheum lhasaense* A. J. Li et P. K. Hsiao, *Rheum hotaoense* C. Y. Cheng et Kao, *Rheum australe* D. Don and *Rheum likiangense* Sam.

In an embodiment of the present invention, in the method for extracting stilbenoid compounds according to the present invention, the solvent is water, methanol, ethanol, acetone or a mixed solvent thereof in any ratio.

In a preferred embodiment of the present invention, in the method for extracting stilbenoid compounds according to the present invention, the solvent is methanol, ethanol or acetone.

In an embodiment of the present invention, in the method for extracting stilbenoid compounds according to the present invention, the solvent has a temperature of 20° C.-40° C.

In an embodiment of the present invention, in the method for extracting stilbenoid compounds according to the present invention, the extracting is performed one to three times.

In an embodiment of the present invention, the extracting is performed one, two or three times.

In a preferred embodiment of the present invention, in the method for extracting stilbenoid compounds according to the present invention, the extracting is performed for 5-10 minutes each time.

According to another aspect of the present invention, an extract rich in stilbenoid compounds prepared according to the above flash extraction method is further provided.

The technical solutions of the present invention at least have one of the following advantages:

The flash extraction method of the present invention is advantageous in simple operation, high extraction speed, short extraction cycle, saved energy consumption needed for heating and cooling, and reduced production costs. Meanwhile, by using the blitzkrieg extraction method of the present invention, stilbenoid compounds are obtained in a significantly higher purity than a traditional method. This facilitates subsequent purification and is suitable for the large scale industrial production of stilbenoid compounds, exhibiting a high application value and development prospect.

DETAILED DESCRIPTION OF EMBODIMENTS

Hereinafter, the technical solutions in embodiments of the present invention will be described clearly and completely in conjunction with examples of the present invention. It is apparent that the described examples are merely part of the present invention rather than all. Based on the examples in the present invention, all other examples obtained by those of ordinary skill in the art without creative work are within the scope of the present invention.

EXAMPLE 1

Extraction of Stilbenoid Compounds in the *Rheum lhasaense* A. J. Li Et P. K. Hsiao Medicinal Material Materials: The *Rheum lhasaense* A. J. Li et P. K. Hsiao medicinal material (purchased from Lhasa, Tibet) was treated by removing impurities, and cleaned and pulverized into coarse powder.

Flash extraction: 100 g coarse powder of the *Rheum lhasaense* A. J. Li et P. K. Hsiao medicinal material was taken, and ethanol was added in a 10-fold volume (W/V, in g/ml). The coarse powders were extracted three times in a flash extractor for three times, and 5 min each time, and filtered. The filtrate was combined and concentrated to dryness, to obtain about 8.9 g of *Rheum lhasaense* A. J. Li et P. K. Hsiao extract.

Extraction under ethanol reflux: 100 g coarse powder of the *Rheum lhasaense* A. J. Li et P. K. Hsiao medicinal material was taken, and ethanol was added in a 10-fold volume (W/V, in g/ml) for extraction under reflux three times for 1 h each and filtered. The filtrate was combined and concentrated to dryness, to obtain about 9.2 g of *Rheum lhasaense* A. J. Li et P. K. Hsiao extract.

Ultrasonic extraction: 100 g coarse powder of the *Rheum lhasaense* A. J. Li et P. K. Hsiao medicinal material was taken, and ethanol was added in a 10-fold volume (W/V, in g/ml) for ultrasonic extraction for three times with 30 minutes each time, and filtered. The filtrate was combined and concentrated to dryness, to obtain about 8.8 g of *Rheum lhasaense* A. J. Li et P. K. Hsiao extract.

EXAMPLE 2

Extraction of Stilbenoid Compounds in the *Rheum likiangense* Sam. Medicinal Material Materials: The *Rheum likiangense* Sam. medicinal material (purchased from Diqing, Yunnan) was treated by removing impurities, and cleaned and pulverized into coarse powder.

Flash extraction: 100 g coarse powder of the *Rheum likiangense* Sam. medicinal material was taken, and ethanol was added in a 10-fold volume (W/V, in g/ml). The coarse powder was extracted for three times in a flash extractor with 5 min each time, and filtered. The filtrate was combined and concentrated to dryness, to obtain about 7.5 g of *Rheum likiangense* Sam. extract.

Extraction under ethanol reflux: 100 g coarse powder of the *Rheum likiangense* Sam. medicinal material was taken, and ethanol was added in a 10-fold volume (W/V, in g/ml) for extraction under reflux for three times with 1 h each time, and filtered. The filtrate was combined and concentrated to dryness, to obtain about 8.4 g of *Rheum likiangense* Sam. extract.

Ultrasonic extraction: 100 g coarse powder of the *Rheum likiangense* Sam. medicinal material was taken, and ethanol was added in a 10-fold volume (W/V, in g/ml) for ultrasonic extraction for three times with 30 minutes each time, and filtered. The filtrate was combined and concentrated to dryness, to obtain about 7.8 g of *Rheum likiangense* Sam. extract.

EXAMPLE 3

Extraction of Stilbenoid Compounds in the *Rheum hotaoense* C. Y. Cheng Et Kao Medicinal Material Materials: The *Rheum hotaoense* C. Y Cheng et Kao medicinal material (purchased from Minhe, Qinghai) was treated by removing impurities, and cleaned and pulverized into coarse powder.

Flash extraction: 100 g coarse powder of the *Rheum hotaoense* C. Y. Cheng et Kao medicinal material was taken, and ethanol was added in a 15-fold volume (W/V, in g/ml). The coarse powder was extracted for three times in a flash extractor with 5 minutes each time, and filtered. The filtrate was combined and concentrated to dryness, to obtain about 6.9 g of *Rheum hotaoense* C. Y Cheng et Kao extract.

Extraction under ethanol reflux: 100 g coarse powder of the *Rheum hotaoense* C. Y. Cheng et Kao medicinal material was taken, and ethanol was added in a 15-fold volume (W/V, in g/ml) for extraction under reflux for three times with 1 h each time, and filtered. The filtrate was combined and concentrated to dryness, to obtain about 7.6 g of *Rheum hotaoense* C. Y. Cheng et Kao extract.

Ultrasonic extraction: 100 g coarse powder of the *Rheum hotaoense* C. Y Cheng et Kao medicinal material was taken, and ethanol was added in a 15-fold volume (W/V, in g/ml) for ultrasonic extraction for three times with 30 minutes each time, and filtered. The filtrate was combined and concentrated to dryness, to obtain about 7.4 g of *Rheum hotaoense* C. Y. Cheng et Kao extract.

EXAMPLE 4

Extraction of Stilbenoid Compounds in the *Rheum australe* D. Don Medicinal Material Materials: The *Rheum australe* D. Don medicinal material (purchased from Lhasa, Tibet) was treated by removing impurities, and cleaned and pulverized into coarse powder.

Flash extraction: 100 g coarse powder of the *Rheum australe* D. Don medicinal material was taken, and ethanol was added in a 10-fold volume (W/V, in g/ml). The coarse powder was extracted for three times in a flash extractor with 10 minutes each time, and filtered. The filtrate was combined and concentrated to dryness, to obtain about 7.3 g of *Rheum australe* D. Don extract.

Extraction under ethanol reflux: 100 g coarse powder of the *Rheum australe* D. Don medicinal material was taken, and ethanol was added in a 10-fold volume (W/V, in g/ml) for extraction under reflux for three times with 1 h each time, and filtered. The filtrate was combined and concentrated to dryness, to obtain about 7.7 g of *Rheum australe* D. Don extract.

Ultrasonic extraction: 100 g coarse powder of the *Rheum australe* D. Don medicinal material was taken, and ethanol was added in a 10-fold volume (W/V, in g/ml) for ultrasonic extraction for three times with 30 minutes each time, and filtered. The filtrate was combined and concentrated to dryness, to obtain about 7.2 g of *Rheum australe* D. Don extract.

EXAMPLE 5

Determination of Stilbenoid Compounds Extracts

Instruments and reagents: Shimadzu UV-2450 UV spectrophotometer, Sartorius CP225D analytical balance, 2,3,5,4'-tetrahydroxyldiphenylethylene-2-O-β-D glucoside control (National Institutes for the Control of Food and Pharmaceuticals, No. 110844-201310).

1. Maximum wavelength: all stilbenoid compounds have a diphenylethylene skeleton structure, and the maximum wavelength is selected as 306 nm in reference to the determination method for diphenylethylene glycosides.

2. Preparation of the control solution: an appropriate amount of 2,3,5,4'-tetrahydroxyldiphenylethylene-2-O-β-D glucoside control was weighted precisely and dissolved by adding an appropriate amount of 95% ethanol, to prepare a solution with a concentration of 0.05 mg/ml as the control solution.

3. Preparation of the test solution: about 0.1 g medicinal material extract from each of Examples 1-4 was taken and precisely weighted, and placed in a flask with plug. 100 mL of 95% ethanol was precisely added and weighted. The solution was ultrasonically treated (power: 250 W; frequency: 35 kHz) for 30 min, allowed to cool, again weighted, complemented for the lost weight with 95% ethanol, shaken up and filtered. 5 ml of the subsequent filtrate was taken precisely into a 25 ml volumetric flask, and dissolved and adjusted to a constant volume with 95% ethanol, as the test solution.

4. Investigation of the linear relationship: the 2,3,5,4'-tetrahydroxyldiphenylethylene-2-O-β-D glucoside control was taken and 95% ethanol was added, to prepare a standard stock solution with a concentration of 0.1 mg/ml for later use. 0.5 ml, 1 ml, 2 ml, 5 ml and 7 ml of the stock solution was taken and placed in a 10 ml volumetric flask respectively, and dissolved and adjusted to a constant volume with 95% ethanol, to prepare a 0.005 mg/ml, 0.01 mg/ml, 0.02 mg/ml, 0.05 mg/ml and 0.07 mg/ml dilution solution. The diphenylethylene glycoside stock solution and dilution solutions with different concentrations were taken and assayed for absorbance, respectively. Linear regressions were calculated with the diphenylethylene glycoside concentration (mg/ml) as the abscissa and the average absorbance as the ordinate, to obtain a linear equation: $Y=6.9336X-0.0028$, $r=0.9992$ ($n=6$).

5. Stability test: the same standard solution was taken precisely and assayed for absorbance 0 h, 0.5 h, 1 h, 2 h and 3 h following preparation respectively, based on which the relative standard deviation was calculated. The results show RSD=3.68% (n=5), suggesting that the test solution is stable and reliable within 3 hours.

6. Repeatability test: the same test solution was assayed continuously for absorbance for seven times and the relative standard deviation was calculated. The results show RSD=0.93%, suggesting a good instrumental repeatability.

7. Reproducibility test: the same medicinal material extract was taken and six portions were weighted at the same time. The extraction treatment was performed in parallel according to the preparation method of the test solution, and the content of stilbenoid compounds was determined. The results show RSD=2.62%, suggesting a good reproducibility of the above extraction method.

8. Determination of the purity of stilbenoid compounds in each sample: 0.1 g of extracts prepared in each of Examples 1-4 were weighted precisely, and the test solution was prepared respectively according to the preparation method of test solutions. The purities stilbenoid compounds were determined. The data results are seen in Table 1.

TABLE 1

The purities of stilbenoid compounds in each extract

| Example | Sample name | Purity % | RSD (%) |
|---|---|---|---|
| Example 1 | *Rheum lhasaense* A. J. Li et P. K. Hsiao extract (flash extraction) | 30.4 | 2.21 |
| | *Rheum lhasaense* A. J. Li et P. K. Hsiao extract (extraction under reflux) | 20.7 | 2.85 |
| | *Rheum lhasaense* A. J. Li et P. K. Hsiao extract (ultrasonic extraction) | 18.6 | 2.93 |
| Example 2 | *Rheum likiangense* Sam. extract (flash extraction) | 25.8 | 1.87 |
| | *Rheum likiangense* Sam. extract (extraction under reflux) | 17.5 | 2.44 |
| | *Rheum likiangense* Sam. extract (ultrasonic extraction) | 17.8 | 2.19 |
| Example 3 | *Rheum hotaoense* C. Y. Cheng et Kao extract (flash extraction) | 26.4 | 2.76 |
| | *Rheum hotaoense* C. Y. Cheng et Kao extract (extraction under reflux) | 16.3 | 2.44 |
| | *Rheum hotaoense* C. Y. Cheng et Kao extract (ultrasonic extraction) | 14.9 | 2.51 |
| Example 4 | *Rheum australe* D. Don extract (flash extraction) | 19.2 | 2.37 |
| | *Rheum australe* D. Don extract (extraction under reflux) | 12.3 | 2.87 |
| | *Rheum australe* D. Don extract (ultrasonic extraction) | 11.4 | 1.94 |

As can be seen from the results in Table 1, four *Rheum* medicinal materials were extracted using different extraction methods under the same solvent condition, and the purities of stilbenoid compounds by flash extraction and extraction under flux are higher. Taking the energy consumption generated during heating, solvent condensing and so on into overall consideration, it can be found that flash extraction shows remarkable advantages in the case of the same extraction rate.

EXAMPLE 6

Selection of a Solvent for Extracting the *Rheum lhasaense* A. J. Li Et P. K. Hsiao Medicinal Material Materials: The *Rheum lhasaense* A. J. Li et P. K. Hsiao medicinal material (purchased from Lhasa, Tibet) was treated by removing impurities, and cleaned and pulverized into coarse powder.

100 g coarse powder of the *Rheum lhasaense* A. J. Li et P. K. Hsiao medicinal material was taken, ethanol, methanol, acetone, ethyl acetate and water were added in a 10-fold volume (W/V, in g/ml) respectively. The coarse powder was extracted for three times in a flash extractor with 5 minutes each time, and filtered. The filtrate was combined and concentrated to dryness. An appropriate amount of extracts were taken and assayed for the purity of stilbenoid compounds according to the method in Example 5, respectively. The results are seen in Table 2.

TABLE 2

The content of stilbenoid compounds in different solvent extracts of *Rheum lhasaense* A. J. Li et P. K. Hsiao

| Solvent for extraction | Purity % | Extract weight (g) | The total amount of stilbenoid compounds (g) |
|---|---|---|---|
| Methanol | 29.2 | 8.9 | 2.6 |
| Ethanol | 30.2 | 8.6 | 2.6 |
| Acetone | 27.8 | 7.9 | 2.2 |
| Water | 22.4 | 9.8 | 2.2 |
| Ethyl Acetate | 15.5 | 7.1 | 1.1 |

As can be seen from the results in Table 2, under different solvent extraction conditions, the extraction rates of stilbenoid compounds by methanol, ethanol or acetone are higher, while the extraction rates by water or ethyl acetate are lower.

EXAMPLE 7

Selection for Times of Exaction of the *Rheum lhasaense* A. J. Li Et P. K. Hsiao Medicinal Material Materials: The *Rheum lhasaense* A. J. Li et P. K. Hsiao medicinal material (purchased from Lhasa, Tibet) was treated by removing impurities, and cleaned and pulverized into coarse powder.

100 g coarse powder of the *Rheum lhasaense* A. J. Li et P. K. Hsiao medicinal material was taken and ethanol was added in a 10-fold volume (W/V, in g/ml), respectively. The coarse powder was extracted for one, two, three, four and five times in a flash extractor with 5 minutes each time and filtered, respectively. The filtrate was combined and concentrated to dryness. An appropriate amount of extract was taken and assayed for the purity of stilbenoid compounds according to the method in Example 5, respectively. The results are seen in Table 3.

TABLE 3

The purity of stilbenoid compounds in the *Rheum lhasaense* A. J. Li et P. K. Hsiao extract under a different extraction frequency

| Times of extraction | Purity % | Extract weight (g) | Total amount of stilbenoid compounds (g) |
|---|---|---|---|
| 1 | 28.9 | 7.9 | 2.28 |
| 2 | 29.6 | 8.4 | 2.49 |
| 3 | 29.4 | 8.4 | 2.47 |
| 4 | 29.8 | 9 | 2.68 |
| 5 | 29.5 | 8.9 | 2.63 |

As can be seen from the results in Table 3, under different times of extraction, the extraction rates of stilbenoid compounds extracted for four times and more are not greatly different from that under extractions for 1 to 3 times. Moreover, the extraction has been almost completed under 1 to 3 times of extraction.

EXAMPLE 8

Selection of Extraction Duration of the *Rheum lhasaense* A. J. Li Et P. K. Hsiao Medicinal Material Materials: The *Rheum lhasaense* A. J. Li et P. K. Hsiao medicinal material (purchased from Lhasa, Tibet) was treated by removing impurities, and cleaned and pulverized into coarse powder.

100 g coarse powder of the *Rheum lhasaense* A. J. Li et P. K. Hsiao medicinal material was taken and ethanol was added in a 10-fold volume (W/V, in g/ml), respectively. The coarse powder was extracted for three times in a flash extractor for 1 minute, 5 minutes, 10 minutes, 15 minutes and 20 minutes each times, and filtered, respectively. The filtrate was combined and concentrated to dryness. An appropriate amount of extracts were taken and assayed for the purity of stilbenoid compounds according to the method in Example 5, respectively. The results are seen in Table 4.

TABLE 4

The purities of stilbenoid compounds in the *Rheum lhasaense* A. J. Li et P. K. Hsiao extract under different times of extraction

| Extraction duration | Content % | Extract weight (g) | The total amount of stilbenoid compounds (g) |
|---|---|---|---|
| 1 minute | 18.8 | 8.3 | 1.56 |
| 5 minutes | 27.8 | 8.5 | 2.36 |
| 10 minutes | 28.6 | 8.7 | 2.49 |
| 15 minutes | 29.3 | 8.6 | 2.52 |
| 20 minutes | 30.1 | 8.7 | 2.62 |

As can be seen from the results in Table 4, for stilbenoid compounds extracted under different extraction durations, the total amount of stilbenoid compounds extracted is higher for 5 minutes and 10 minutes, and lower for 1 minute.

EXAMPLE 9

Selection of Solvent Temperature for Extracting the *Rheum lhasaense* A. J. Li Et P. K. Hsiao Medicinal Material Materials: The *Rheum lhasaense* A. J. Li et P. K. Hsiao medicinal material (purchased from Lhasa, Tibet) was treated by removing impurities, and cleaned and pulverized into coarse powder.

100 g coarse powder from the *Rheum lhasaense* A. J. Li et P. K. Hsiao medicinal material was taken, and ethanol with a temperature of 20° C., 30° C., 40° C., 50° C., 60° C. or 70° C. was added in a 10-fold volume (W/V, in g/ml), respectively. The coarse powder was extracted twice in a flash extractor with 15 minutes each time, and filtered. The filtrate was combined and concentrated to dryness. An appropriate amount of extracts were taken and assayed for the purities of stilbenoid compounds according to the method in Example 5, respectively. The results are seen in Table 5.

TABLE 5

The purities of stilbenoid compounds in the *Rheum lhasaense* A. J. Li et P. K. Hsiao extract under different solvent temperatures

| Extraction duration | Purity % | Extract weight (g) | total amount of stilbenoid compounds (g) |
|---|---|---|---|
| Extraction at 20° C. | 29.5 | 8.8 | 2.60 |
| Extraction at 30° C. | 30.1 | 8.7 | 2.62 |
| Extraction at 40° C. | 29.3 | 8.9 | 2.61 |
| Extraction at 50° C. | 24.7 | 10.6 | 2.62 |
| Extraction at 60° C. | 23.4 | 11.3 | 2.65 |
| Extraction at 70° C. | 22.7 | 11.6 | 2.63 |

As can be seen from the results in Table 5, when the extraction is performed under the same condition, stilbenoid compounds of a higher purity can be obtained at a solvent temperature of 20° C. to 40° C., while the purity is decreased at a temperature above 50° C. This is possibly due to increase of solubility of each component and increase in the incorporation of various impurities after the solvent temperature is raised.

The invention claimed is:

1. A method for extracting stilbenoid compounds, comprising:
   (a) providing a medicinal material rich in stilbenoid compounds as a raw material,
   (b) extracting the medicinal material with a flash extractor one or more times,
   (c) filtering the extract made in step (b) after each extraction,
   (d) combining the filtrates when there are two or more filtrates and
   (e) drying the filtrate or combined filtrates to concentrate the stilbenoid compounds.

2. The method according to claim 1, comprising:
   (a) providing a medicinal material rich in stilbenoid compounds as a raw material,
   (b) pulverizing the medicinal material,
   (c) adding a solvent to the pulverized material,
   (d) extracting the pulverized material one to four times with a flash extractor for 5-20 minutes each time,
   (e) filtering the extract made in step (d) after each extraction,
   (f) combining the filtrates when there are two or more filtrates and
   (g) drying the filtrate or combined filtrates to concentrate the stilbenoid compounds.

3. The method according to claim 1, wherein the medicinal material rich in stilbenoid compounds is one of *Rheum lhasaense* A. J. Li et P. K. Hsiao, *Rheum hotaoense* C. Y Cheng et Kao, *Rheum australe* D. Don and *Rheum likiangense* Sam., or a mixture thereof.

4. The method according to claim 2, wherein the solvent is water, methanol, ethanol, acetone or a mixture thereof, wherein, in the mixture, the solvents may be in any ratio.

5. The method according to claim 2, wherein the solvent is methanol, ethanol or acetone.

6. The method according to claim 2, wherein the temperature of the solvent is 20° C. to 40° C.

7. The method according to claim 1, wherein the extracting is performed one to three times.

8. The method according to claim 1, wherein the extracting is performed for 5-10 minutes each time.

9. The method according to claim 2, wherein the weight-to-volume ratio of the medicinal material to the solvent is 1:10 to 1:15.

* * * * *